(12) United States Patent
Clothier

(10) Patent No.: US 8,465,979 B2
(45) Date of Patent: Jun. 18, 2013

(54) METHOD FOR DETECTING TIN

(75) Inventor: Brent Allen Clothier, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 258 days.

(21) Appl. No.: 13/033,983

(22) Filed: Feb. 24, 2011

(65) Prior Publication Data

US 2012/0216827 A1 Aug. 30, 2012

(51) Int. Cl.
*G01N 33/20* (2006.01)

(52) U.S. Cl.
USPC .......................................................... 436/77

(58) Field of Classification Search
USPC .......................................................... 436/77
See application file for complete search history.

(56) References Cited

U.S. PATENT DOCUMENTS

| 4,886,552 A | 12/1989 | Jaworowski et al. |
| 5,993,559 A | 11/1999 | Singer et al. |
| 2010/0147481 A1 | 6/2010 | Kool et al. |

FOREIGN PATENT DOCUMENTS

| CN | 101430285 A | 5/2009 |

OTHER PUBLICATIONS

Michelle E. Gange, Simon C. Parratt, Philip Jones, Paul S. Francis and Neil W. Barnett; Chemiluminescence from the reaction of tin(II) with tris(2,20-bipyridyl)ruthenium(III); 2009, 134, pp. 2397-2399.
Richard D. Gerardi, Neil W. Barnett, Phillip Jones; Two chemical approaches for the production of stable solutions of tris(2,20-bipyridyl)ruthenium(III) for analytical chemiluminescence; Analytica Chimica Acta 388 (1999); pp. 1-10.
EP Search Report 12156530, Nov. 12, 2013.
M. E. Gange et al., "Chemiluminescence from the reaction of tin(II) with Tris (2,2'-bipyridyl)ruthenium(III)," The Journal of the Royal Society of Chemistry, vol. 134, pp. 2397-2399, 2009.
"A New Photosensitizer, Tris(2,2'-bipyriding)ruthenium(II) Chloride," Journal of the American Chemical Society. Vol. 93, No. 7, pp. 1800-1801, Apr. 7, 1971.
L. Hu et al., "Applications and trends in electrochemiluminescence," Chemical Society Reviews, vol. 39, pp. 3275-3304, 2010.
L. Guo et al., "Mechanism study on inhibted Ru(bpy)32+ electrochemilinescence between coreactants," Physical Chemistry Chemical Physics, vol. 12, pp. 12826-12832, 2010.

*Primary Examiner* — Krishnan S Menon
*Assistant Examiner* — Dwan A Gerido
(74) *Attorney, Agent, or Firm* — Paul J. DiConza

(57) ABSTRACT

A method for the detection of tin is presented. A specimen is first contacted with a ruthenium-containing species to create a contacted region of the specimen. At least a portion of the contacted region is then irradiated by an excitation radiation and monitored for a relaxation radiation emitted in response to the excitation radiation.

20 Claims, 1 Drawing Sheet

METHOD FOR DETECTING TIN

BACKGROUND OF THE INVENTION

The invention relates generally to a method for detecting tin, and more specifically to a method for detecting tin on surfaces of cast articles, for example, turbine engine components.

Liquid metal cooling is often used to form high-gradient castings of superalloy components in advanced gas turbines, as well as other industrial parts. A molten metallic bath used for the cooling, generally, includes tin. During the cooling process, some of the molten metal can breach the casting container and deposit on the surfaces of a cast article as a contaminant. The cast article is typically subjected to a series of thermal fabrication and heat treatment cycles before becoming a useful article. In certain demanding applications, for example gas turbine engine airfoils, the presence of even trace amounts of low melting residual metal, usually tin, may have severe negative impact upon the surface quality and high temperature properties of the article.

Various cleaning methods are used to remove tin contamination. One example is grit blasting followed by etching in a chemical bath. These two processes are effective in removing most of the tin. However, thin residual layers may remain. These residual layers are poorly discernable to the naked eye. The use of advanced coating removal (ACR) baths has also been proven to be highly effective to remove tin. However, confirmation of tin removal is critical to subsequent processing.

Different processes, chemical or non-chemical, have been proposed to detect residual tin. For example, on heating at a high temperature, residual tin, if present, transforms into a tan-colored matter that can be easily seen with the naked eye. In this process, articles are subjected to a costly and time-consuming heating process needlessly if they had no residual tin. Other detection processes, such as use of an X-ray fluorescence analyzer, a colorimetric reagent provide ability to visualize residual tin immediately after cleaning process. However, most of these methods are either very expensive, complicated or include reagents that may damage the article surface.

Accordingly, there is a need for methods that enable quick and inexpensive detection of tin. It would also be desirable if the method does not result in the formation of an unacceptable amount of hazardous matter. For example, the method should effectively detect tin while substantially preserving the article.

BRIEF DESCRIPTION

Embodiments of the invention are directed towards a method for the detection of tin.

In some embodiments, a method includes the step of contacting a specimen with a ruthenium-containing species to create a contacted region of the specimen. In following steps, at least a portion of the contacted region is irradiated by an excitation radiation and monitored for a relaxation radiation emitted in response to the excitation radiation.

In some other embodiments, a method is provided for detecting the presence of tin on a surface of an article. The method includes the steps of applying a solvating solution and a solution of ruthenium (III)-ligand complex on the surface to create a contacted region of the article. The solvating solution comprises a halide. A portion of the contacted region is then irradiated by an excitation radiation comprising ultraviolet radiation, and monitored for a relaxation radiation emitted in response to the excitation radiation.

DRAWINGS

These and other features, aspects, and advantages of the present invention will become better understood when the following detailed description is read with reference to the accompanying drawings, wherein.

DETAILED DESCRIPTION

Figure 1:
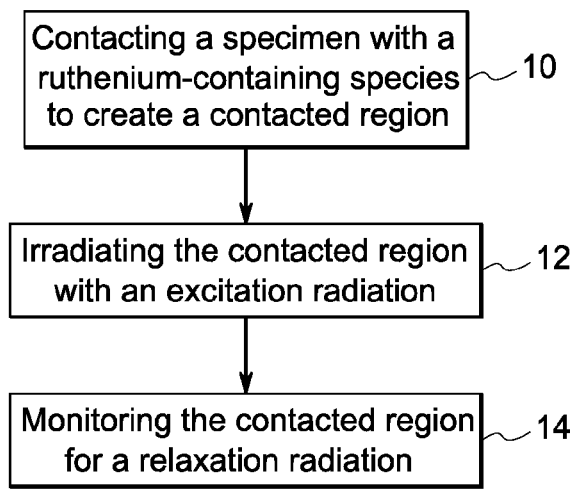
FIG. 1 is a flow diagram depicting a method for detecting tin, in accordance with an embodiment of the invention.

As used herein, the term ""superalloy"" refers to a nickel-based, cobalt-based, or iron-based heat resistant alloy that has superior strength and oxidation resistance at high temperatures. Nickel-based and cobalt-based alloys are favored for high-performance applications. The superalloy can contain chromium to impart surface stability and one or more minor constituents such as molybdenum, tungsten, titanium, iron or aluminum for strengthening purposes. Physical properties of the superalloy make the superalloy particularly useful for manufacturing a gas turbine component.

During a casting process, as discussed earlier, a cast article may become contaminated due to deposition of tin on the surfaces of the cast article. Various methods or techniques can be used to strip the deposited tin from the surfaces of the cast article. Even after effective cleaning or stripping processes, there is a possibility of traces of residual tin to be present on the surface. As fully cleaned articles or components are desired, it is necessary to determine if the surfaces of the article are cleaned or still contain residual tin. To ensure quality of the cast article, a detection test is performed to confirm the presence or absence of any tin on the surfaces, according to one embodiment of the present invention. A selective indicator, which fluoresces upon contact with tin, may be used. The response of the indicator assures the presence or the absence of any tin traces on the surfaces.

As used herein, the term ""selective indicator"" refers to a species that gives an optical response on reacting with tin. In one embodiment, the selective indicator comprises a ruthenium (Ru)-containing species. The optical response of the indicator can typically be observed through chemiluminescence in the visible region of the electromagnetic radiation. ""Chemiluminescence"" is luminescence where excitation energy is supplied by chemical reactions.

According to some embodiments of the invention, the ruthenium-containing species may be specified as Ru(III)-ligand complex. The ligands may be selected from the group consisting of bipyridine, phenanthroline, bipyrazine, terpyridine, and triazine. Non-limiting examples of the ligands may include 2,2'-bipyridine; 4,4'-dimethylbipyridine; 4,4'-biphenyl-2,2'-bipyridine; 1,10-phenanthroline; 4,7-dimethyl-1,10-phenanthroline; 2,2'-bipyrazine; 2,2',2''-terpyridine; and 2,4,6-tripyridyl-2-triazine. In certain embodiments, the ruthenium-containing species may include tris(2,2'-bipyridyl)dichloro ruthenium(III).

Quite generally, in the interest of brevity of the discussions herein, tris(2,2'-bipyridyl)dichloro ruthenium(III) and tris(2,2'-bipyridyl)dichloro ruthenium(II) may be referred to as $Ru^{III}(bipy)_3^{2+}$ and $Ru^{II}(bipy)_3^{2+}$, respectively.

These ruthenium-containing species often show high chemiluminescent selectivity for tin. For example, the selectivity of tris(2,2'-bipyridyl) dichloro ruthenium(III) stems from its ability to oxidize Sn(II) into a highly-reactive and unstable intermediate Sn(III) by enabling a Ru(III)-Sn(II) redox reaction. The redox reaction results in the emission of a chemiluminescence. However, the chemiluminescence from the Ru(III)-Sn(II) redox mechanism is very short for practical visualization by the naked eye.

Most of the embodiments of the invention provide a method for detecting tin using the ruthenium-containing species. The method involves the steps as illustrated in flow diagram of FIG. 1. Step 10 provides a specimen to contact with the ruthenium-containing species to create a contacted region of the specimen. At least a portion of the contacted region is irradiated with an excitation radiation and monitored for a relaxation radiation emitted in response to the excitation radiation in step 12 and 14, respectively.

Some embodiments provide a method for detecting the presence of tin on a surface of an article. The article may be a casting of a metal, or a metal alloy. In one embodiment, the article includes iron, cobalt, nickel, aluminum, chromium, titanium, and mixtures or alloys, for example, stainless steel. In a specific embodiment, the article includes a superalloy. The casting can be of any shape. In one embodiment, the cast article is a component of a turbine engine, for example, an airfoil, a blade or a bucket.

The ruthenium-containing species often comprises a dilute solution of the ruthenium (III)-ligand complex. The preparation of the Ru(III)-ligand complex solution is conducted by dissolving a Ru(III)-ligand complex in an acid. Non-limiting examples of suitable acids may include sulfuric acid, hydrofluoric acid, hydrochloric acid, phosphoric acid, nitric acid, boric acid, and carboxylic acid. In certain instances, diluted sulfuric acid is most desirable. For example, a dilute solution of $Ru^{III}(bipy)_3^{2+}$ dissolved in dilute (for example, about 0.05M) sulfuric acid, is generally used. The concentration of Ru(III)-ligand complex solution for tin detection can be exceptionally dilute, often, less than about 0.01M. In certain instances, the concentration of Ru(III)-ligand complex ranges from about 0.001M to about 0.005M in the solution. The ability to use very dilute solutions of Ru(III)-ligand complex is favorably important given the high cost of ruthenium.

In one embodiment, the method further includes contacting the specimen with a solvating solution to solvate any tin present on the surface of the specimen. In some embodiments, the solvating solution may be included in the Ru(III)-ligand complex solution. In other embodiments, the solvating solution may be applied on the surface prior to contacting the with the Ru(III)-ligand complex solution.

The solvating solution is a mild acidic solution that comprises a halide. The presence of the halide stabilizes Sn(II) by preventing its precipitation as a hydroxide or oxyhyroxide. In one embodiment, the halide comprises a fluoride, a chloride, a bromide, an iodide or a combination thereof. In a particular embodiment, the halide may be an alkali halide that often includes Group 1A elements. Sodium fluoride is one example of an alkali halide. The solvating solution is usually buffered to maintain a pH optimal for the ruthenium-containing species to activate a redox reaction as discussed above. In some instances, the solution is adjusted to pH between about 3 and about 6.

As discussed in some of the above embodiments, the solvating solution may be first applied on the surface of the specimen. After a period of time, the Ru(III)-ligand complex solution is applied on top of the solvating solution and thereby creates a contacted region of the specimen. Both the solutions may be applied lightly to generate thin and static wet films on the surface of the specimen to prevent dripping and running.

Various techniques can be used to apply these solutions. In one embodiment, the solutions may be applied by using a coating technique. Examples of suitable techniques include dip-coating, spin coating and spraying. Other techniques may include painting the surface with the solutions, pouring the solutions over the surface or the like.

In one embodiment, an amount of residual tin may be present on a portion of the contacted region of the specimen. In these instances, the solvating solution stabilizes the residual tin in Sn(II) form. The Ru(III)-ligand complex solution reacts with Sn(II) and initiates a Ru(III)-Sn(II) redox reaction. The Ru(III)-Sn(II) redox reaction is given below, in an exemplary embodiment.

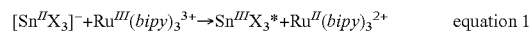   equation 1

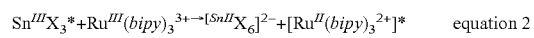   equation 2

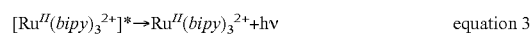   equation 3 where X=F, Cl, Br, or I, and * represents a compound in an electronically excited state.

The $Ru^{III}(bipy)_3^{3+}$ oxidizes Sn(II) into a highly-reactive and unstable intermediate Sn(III) as described in equation 1. This intermediate Sn(III) may reduce $Ru^{III}(bipy)_3^{3+}$ into an electronically-excited $[Ru^{II}(bipy)_3^{2+}]*$ in equation 2. Relaxation of the excited state to ground state results in the emission of an orange chemiluminescence as per equation 3. However, despite emission in the visible range, the orange chemiluminescence is typically too fast for registration by the naked eye. In addition to the chemiluminescence, equation 3 further provides a by-product, $Ru^{II}(bipy)_3^{2+}$ i.e. a Ru(II)-ligand complex. The by-product, Ru(II)-ligand complex may be a luminophore. In these instances, the contacted region comprises the luminophore, Ru(II)-ligand complex.

As used herein, "luminophore" refers to an atom or atomic grouping in a chemical compound that manifests photoluminescence. Luminophores can be divided into two subcategories: fluorophores and phosphors. The difference between luminophores belonging to these two subcategories is derived from the nature of the excited state responsible for the emission of photons. Some luminophores, however, cannot be classified as being exclusively fluorophores or phosphors. Such cases include transition metal complexes (such as ruthenium tris-2,2'-bipyridine) whose luminescence comes from an excited (nominally triplet) metal-to-ligand charge transfer (MLCT) state.

In another embodiment, a portion of the contacted region may not contain any tin present on the surface. In these instances, no redox reaction occurs in absence of tin after completion of step (i) and no luminophore may be present at the contacted region of the specimen. Instead, the portion of the contacted region comprises the Ru(III) ligand complex, which is not a photoluminescent material.

In step (ii), the contacted region is irradiated with an excitation radiation. The wavelength of the applied excitation radiation may depend on the luminophore produced as the by-product of the redox reaction in order to maximize the emission intensity. In certain instances, ultraviolet radiation may be used to illuminate the contacted region of the specimen. Step (ii) is then followed by monitoring the contacted region for a relaxation radiation emitted in response to the excitation radiation in step (iii).

Figure 2:
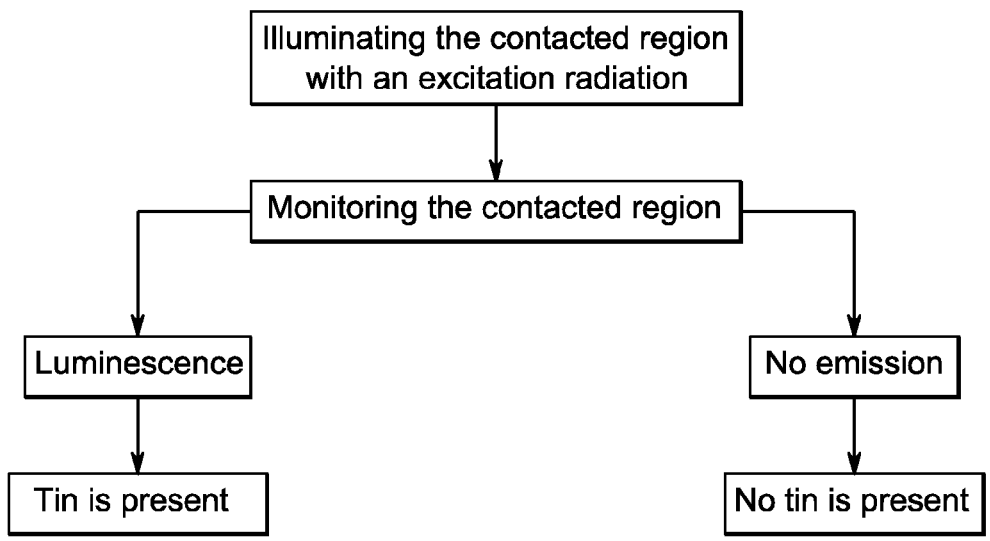
FIG. 2 is a flow diagram depicting a method for detecting tin on a surface of an article, in accordance with another embodiment of the invention.

In one embodiment, a luminescence may be observed on illumination of the contacted region. The luminophore present in the portion of the contacted region produces luminescence in response to the excitation radiation. In an exemplary embodiment, the $[Ru^{II}(bipy)_3^{2+}]*$ produces orange emission when excited with ultraviolet radiation. This luminescence indicates the presence of tin in the portion of the contacted region. In contrast, no emission may be observed in response to the excitation radiation, in another embodiment. No response from a portion of the contacted region indicates the absence of tin in the portion. FIG. 2 illustrates such embodiments in a flow chart.

EXAMPLES

The example that follows is merely illustrative, and should not be construed to be any sort of limitation on the scope of the claimed invention.

Example 1

Preparation of Solution 1

A 250-milliliter beaker was fitted with a stir bar and placed on a stirrer. 0.210 grams of sodium fluoride, and 0.410 grams of sodium acetate were weighed and transferred to the beaker. 75 milliliters of deionized water was added to the beaker with continuous stirring. The solution was allowed to stir for about 15 minutes. Glacial acetic acid was added drop-wise under stirring until a pH of the solution measured 5. Deionized water was further added to make 100-milliliter solution.

Preparation of Solution 2

A 250-milliliter Erlenmeyer flask was fitted with a stir bar and placed on a stirrer/hot plate. 0.267 milliliters of sulfuric acid was poured into the flask. 100 milliliters of deionized water was added (with stir bar spinning slowly) to the flask to prepare a 0.05M sulfuric acid solution. 0.1497 grams of $Ru^{II}(bipy)_3^{2+}$ was dissolved in the sulfuric acid solution. The resulting solution exhibited a vibrant orange color. About 0.95 grams of lead(IV) oxide was added into the solution under aggressive stirring. After about 15 minutes, the color of the solution changed from orange to green, indicating the oxidation of Ru(II) to Ru(III). Because Ru(III) will slowly degrade back to Ru(II), the oxidized solution was used immediately after generation. Alternatively, a continuously-recirculating system can be arranged to maintain the solution in a fully-oxidized state. To filter the green solution free from suspended lead(IV) oxide, a plastic syringe was used to draw out aliquots, when needed.

Tin detection on nickel superalloy surface

A ⅛" thick specimen of nickel superalloy casting was first ultrasonicated for about 15 minutes each in acetone and 2-propanol. A thin layer of about 0.1 mm thickness of tin was electroplated onto a surface of the specimen through a stenciled epoxy (Epotek 301-2) layer. The epoxy was removed by ultrasonicating in acetone and 2-propanol, leaving a patterned tin layer on the surface as shown in FIG. 3. Solution 1 was sprayed onto the surface and the specimen was tilted to drain off excess fluid. The surface was then allowed to dry for about 10 minutes. Solution 2 was then sprayed on to the surface, resulting an immediate conversion of green Ru(III) to orange Ru(II). When the surface was illuminated by ultraviolet radiation (about 365 nm), the patterned letters were readily seen in bright orange color.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for detecting the presence of tin, comprising the steps of:
   (i) contacting a specimen with a ruthenium-containing species to create a contacted region of the specimen;
   (ii) irradiating at least a portion of the contacted region with an excitation radiation; and
   (iii) monitoring the contacted region for a relaxation radiation emitted in response to the excitation radiation.

2. The method of claim 1, wherein irradiating comprises illuminating the contacted region with ultaviolet radiation.

3. The method of claim 1, wherein the specimen comprises a material selected from the group consisting of iron, cobalt, nickel, aluminum, chromium, titanium, and a combination thereof.

4. The method of claim 1, wherein the specimen comprises a superalloy material.

5. The method of claim 1, wherein the specimen comprises a cast article.

6. The method of claim 1, wherein the cast article is an airfoil.

7. The method of claim 1, wherein contacting step comprises reacting the ruthenium-containing species with tin from the specimen to form a luminophore.

8. The method of claim 7, wherein the luminophore comprises a ruthenium(II)-ligand complex.

9. The method of claim 1, wherein the contacting step comprises contacting the specimen with a solution of a ruthenium (III)-ligand complex in an acid.

10. The method of claim 9, wherein the ruthenium(III)-ligand complex comprises a ligand selected from the group consisting of bipyridine, phenanthroline, bipyrazine, terpyridine, and triazine.

11. The method of claim 9, wherein the ruthenium(III)-ligand complex comprises bipyridine.

12. The method of claim 9, wherein the acid comprises sulfuric acid, hydrofluoric acid, hydrochloric acid, phosphoric acid, nitric acid, boric acid, a carboxylic acid or a combination thereof.

13. The method of claim 9, wherein the concentration of the ruthenium(III)-ligand complex is less than about 0.01M in the solution.

14. The method of claim 1, wherein the contacting step further comprises contacting the specimen with a solvating solution.

15. The method of claim 14, wherein contacting the specimen with a solvating solution is performed prior to contacting a specimen with a ruthenium-containing species.

16. The method of claim 14, wherein the solvating solution has a pH in a range from about 3 to about 6.

17. The method of claim 14, wherein the solvating solution comprises a halide.

18. The method of claim 17, wherein the halide comprises a fluoride, a chloride, a bromide, an iodide or a combination thereof.

19. The method of claim 17, wherein the halide comprises an alkali halide.

20. A method for detecting the presence of tin on a surface of an article, comprising the steps of:
    applying an acidic solvating solution on the surface of the article, the solvating solution comprising a halide;
    applying a solution of ruthenium (III)-ligand complex on the surface to create a contacted region of the article;

irradiating at least a portion of the contacted region with an excitation radiation comprising ultraviolet radiation, and monitoring the contacted region for a relaxation radiation emitted in response to the excitation radiation.

* * * * *